United States Patent [19]

Schmoegner et al.

[11] Patent Number: 5,022,898
[45] Date of Patent: Jun. 11, 1991

[54] EXHAUST FILTER SYSTEM FOR STERILIZERS

[75] Inventors: John C. Schmoegner, Redondo Beach; Danny L. Baldoz, Carson, both of Calif.

[73] Assignee: MDT Corporation, Torrance, Calif.

[21] Appl. No.: 463,442

[22] Filed: Jan. 11, 1990

[51] Int. Cl.$^5$ ............................................. B01D 53/00
[52] U.S. Cl. .................................. 55/210; 55/316; 55/387
[58] Field of Search ........................ 55/210, 316, 387

[56] References Cited

U.S. PATENT DOCUMENTS

| | | | |
|---|---|---|---|
| 2,526,782 | 10/1950 | Thorpe | 55/387 |
| 2,930,445 | 3/1960 | Glass et al. | 55/316 |
| 2,965,936 | 12/1960 | Kaye | 422/292 |
| 3,163,494 | 12/1964 | Kaye | 422/30 |
| 3,186,148 | 6/1965 | Merrill et al. | 55/387 |
| 3,464,186 | 9/1969 | Hankison et al. | 55/316 |
| 3,705,480 | 12/1972 | Wireman | 55/316 |
| 3,796,025 | 3/1974 | Kasten | 55/387 |
| 3,941,573 | 3/1976 | Chapel | 55/316 |
| 4,026,685 | 5/1977 | Grix | 55/316 |
| 4,457,892 | 7/1984 | Young | 422/2 |
| 4,673,419 | 6/1987 | Kojima | 55/387 |
| 4,746,338 | 5/1988 | Williams | 55/316 |
| 4,865,637 | 9/1989 | Gruber | 55/316 |

FOREIGN PATENT DOCUMENTS 2146549 4/1985 United Kingdom ................. 55/387

*Primary Examiner*—Jay H. Woo
*Assistant Examiner*—C. Scott Bushey
*Attorney, Agent, or Firm*—Trask, Britt & Rossa

[57] ABSTRACT

A filter system for the exhaust stream of a chemical sterilizer includes a liquid trap filter directly upstream from a canister filter and proximity switch for monitoring the presence or absence of the canister filter.

14 Claims, 2 Drawing Sheets

EXHAUST FILTER SYSTEM FOR STERILIZERS

BACKGROUND OF THE INVENTION

1. Field

The invention relates to sterilizers of the type used in the fields of medicine, dentistry and biological sciences. It is particularly directed to the vent stream (emissions) from such sterilizers and provides an exhaust (vent) filter system of general application but of particular use with chemical vapor sterilizers.

2. State of the Art

The potential health hazards associated with the discharge of exhaust emissions from sterilizer systems and apparatus are well recognized. Chemical vapor sterilization, as widely practiced, involves the exposure of biologically contaminated articles to chemical vapors in a sterilization chamber. At the termination of the sterilization procedure, the vapors are collected and reclaimed, but traces of potentially harmful vapors and/or gases may remain in the chamber and its contents.

It has been the practice in large-scale equipment to purge the chamber of such residual vapors by directing a stream of air or other purge gas, such as nitrogen, through the chamber. The residual chemical sterilant is thereby swept from the chamber in an exhaust or vent stream. The vent stream is composed of fluids, composed primarily of gases, but often including vaporous constituents which tend to condense upon cooling. More recently, purging is practiced in smaller scale equipment as well.

Particularly in the case of smaller scale sterilization equipment, discharge of the vent stream may be directly into the interior of a room. If the room is small and poorly ventilated, the possibility exists that unacceptable levels of chemical irritants, e.g. formaldehyde, may accumulate in the room over a prolonged period. One expedient for reducing or eliminating this possibility is to filter or chemically neutralize the vent fluids prior to their discharge into the atmosphere. The presence of condensible vapors in the vent fluids interferes with such procedures. Condensation blocks filter passages and accelerates deterioration of many filter media Moreover, proper maintenance and replacement of filters, while essential, has not been reliably practiced, largely due to inadequate monitoring procedures.

There remains a need for an improved exhaust filter system for chemical and other sterilizer systems.

SUMMARY OF THE INVENTION

This invention provides an improved exhaust system for the vent stream of sterilization apparatus, particularly chemical vapor sterilizers. A receptacle associated with the sterilizer is adapted to receive a disposable canister. A proximity switch or equivalent operably associated with the receptacle senses the presence or absence of the canister.

The receptacle includes a structural base support which is ordinarily, but not necessarily, oriented approximately horizontally. The canister is mounted to one surface of the base, usually in upstanding relationship. A fixture opposite the canister directs vent fluids through the structural base into the canister. The fixture includes a housing which opens through the structural base and contains a liquid trap filter element. Condensed vent fluids are trapped by this filter element, thereby preventing their entry into the canister.

Sterilization equipment is typically operated in cycles. A purge step constitutes the last portion of the cycle. Venting of the sterilization apparatus to the atmosphere is usually done only in connection with the purge. The number of cycles (purges) exhausting through the canister may be counted electronically by well-known circuitry activated by the positioning of the canister on the receptacle. Removal of the canister desirably disables the venting capability of the sterilization apparatus. Both the counting and the disabling functions are controlled by the aforementioned proximity switch.

BRIEF DESCRIPTION OF THE DRAWINGS

In the drawings, which illustrate what is presently regarded as the best mode for carrying out the invention.

DESCRIPTION OF THE ILLUSTRATED EMBODIMENT

Figure 1:
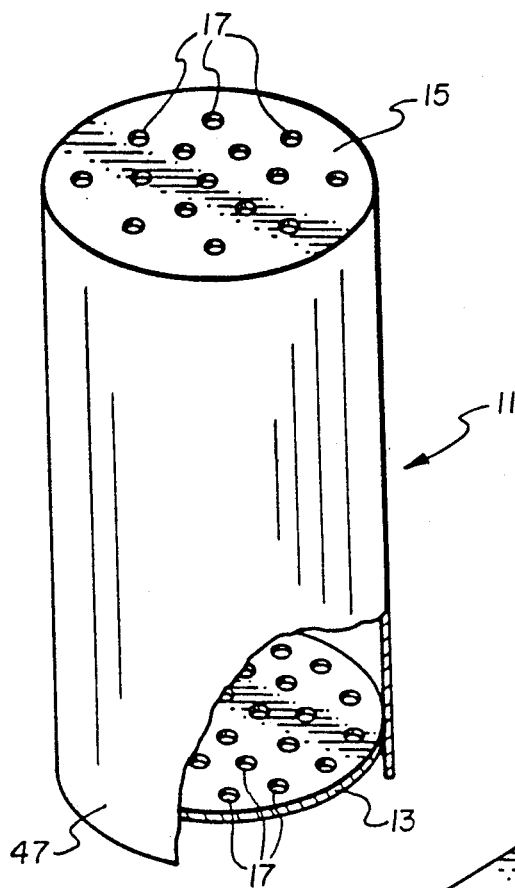
FIG. 1 is a pictorial view of a filter canister of the invention.

The canister 11 illustrated by FIG. 1 is approximately cylindrical with a recessed inlet end 13 and an opposite outlet end 15. Both ends 13, 15 are perforated with apertures 17. The canister 11 is filled with filter medium 18, e.g. activated charcoal, silica gel or other conventional reactive or inert chemical compositions suitable for detoxifying or capturing the exhaust (vent) gases from a sterilization apparatus. Alumina (e.g. ⅛ inch pellets) activated with potassium permanganate (typically about 4 to about 6 percent by weight) is presently regarded as a preferred filter medium for the vent streams of chemical sterilization systems. This medium is effective in removing trace emissions of formaldehyde, for example, from the fluids vented by a chemical vapor sterilizer, such as the MDT® HARVEY® CHEMICLAVE® sterilizers sold by MDT Corporation of Torrance, Calif.

Figure 3:
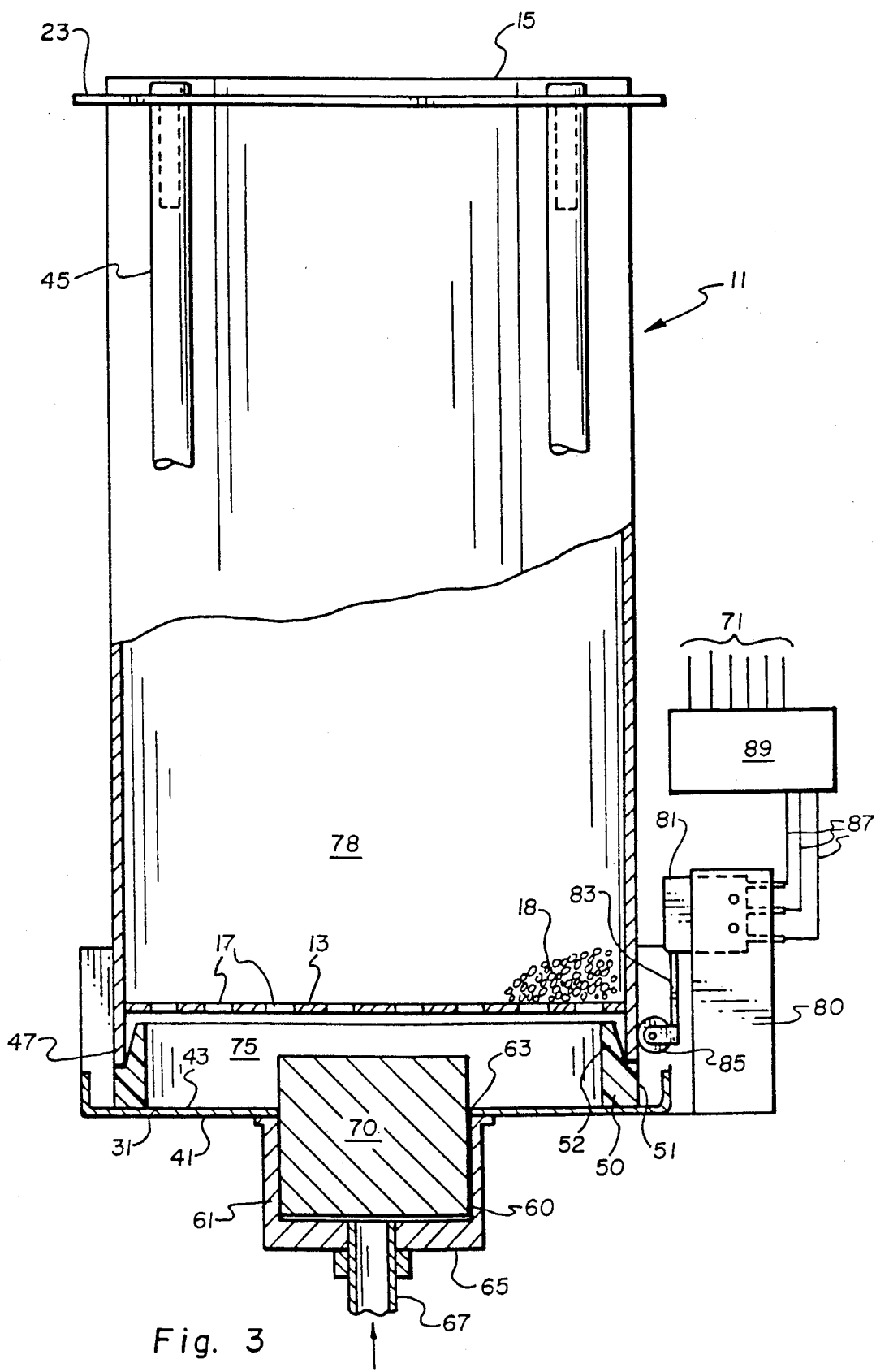
FIG. 3 is a view in elevation, partially in section, illustrating the components of FIGS. 1 and 2 in assembled condition, a portion of those components being illustrated in alternative form.

The canister 11 is configured to slide through an opening 21 through the top plate 23 of a receptacle, designated generally 25. The receptacle also includes a support base 31 which constitutes a portion of a mounting bracket, designated generally 33. The receptacle may be mounted to the sterilization equipment (not shown) by means of mounting holes 35 provided in the top plate 23 and the side support plate 37. The base includes a first (as illustrated, bottom, FIG. 3) mounting surface 41 and a second (top) mounting surface 43 (FIG. 3). The bracket posts 45 function as guide supports to register the sidewall 47 of the canister 11 adjacent the recessed inlet end 13 with a sealing ring 50 positioned on the second (top) mounting surface 43.

Although it is within contemplation that the components of the invention take various configurations, the cylindrical components illustrated are generally preferred. Thus the sealing ring 50 is illustrated as including cylindrical segments 51, 52 which effect a fluid-tight seal with the canister sidewall 47 as best illustrated by FIG. 3. The seal 50 is typically of elastomeric (e.g., rubber) or other resilient material. It is shown concentrically mounted with respect to a well 60 constituting the internal volume of an inlet chamber 61. The well 60 has a top 63, which openly communicates through the support base 31, and a bottom 65. A vent tube conduit 67 openly communicates with the well 60 through its bottom 65 and constitutes means for delivering vent fluids to the well 60.

Figure 2:
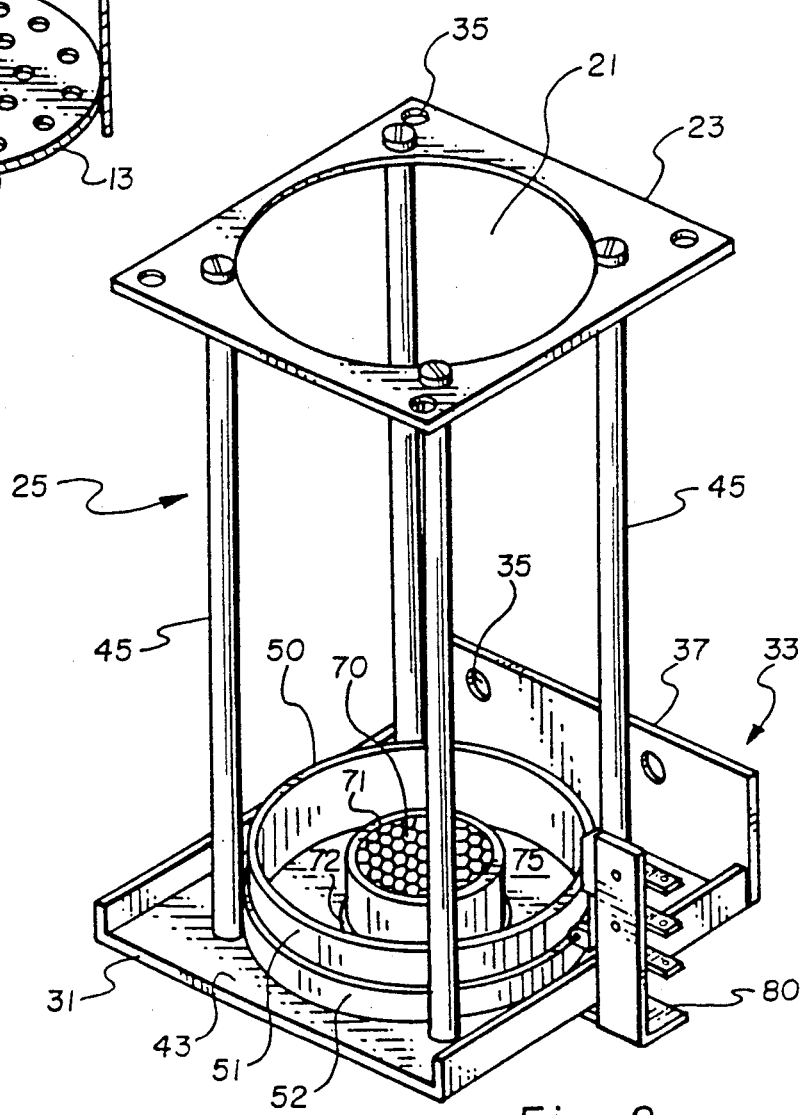
FIG. 2 is a pictorial view of support structure and other components of the invention.

A liquid trap filter element 70, which is typically formed of a sponge-like substance such as cellular foam, (open cell low-to-medium density polyurethane being presently preferred), occupies substantially the entire internal volume of the well 60. As illustrated by FIG. 2, the liquid trap filter 70 is contained within a cylindrical housing 71 which is sealed to the structural base 31 by means of a gasket 72. Alternatively, the filter 70 may comprise a single sponge element inserted into the well 60 as illustrated by FIG. 3. In either event, the filter element 60 may extend above the structural base 31 into an enclosure 75 formed by the canister wall 47, the perforated canister inlet end 13 and the second mounting surface 43 of the structural base 31, as well as the sealing ring 50, if present.

In operation, vent fluids (the gaseous and/or vaporous emissions from a sterilizer apparatus) are introduced through the vent tube 67 to the well 60. Such venting is typically associated with the purging of a sterilizer chamber following a sterilization procedure. The travel path of the vent fluids is through the liquid trap filter 70 into the enclosure 75, within which they collect for entry into the interior 78 of the canister 11. The travel path of the vent stream is then from the canister inlet 13 through the medium 18 and out the canister outlet 15, eventually to the atmosphere. In most instances, discharge from the canister outlet 15 may be directly to the interior of a room, particularly if the room is ventilated.

Liquids, (typically resulting from the condensation of vapors in the vent fluids), entering the well 60 are trapped by the filter element 70. At the end of the operation (e.g. a purge cycle) generating the vent fluids, the entrapped liquids drain by gravity flow from the well 60 through the vent tube 67 for collection or other disposition.

A structural support 80 associated with the structural base 31 carries a proximity switch 81. As illustrated, the switch is actuated by a lever arm 83 which carries a roller 85 at its distal end. The switch 81 is actuated between first and second modes, depending upon whether the canister 11 is positioned on the second mounting surface 43 as illustrated by FIG. 3 or is removed as illustrated by FIG. 2. The switch 81 is operably associated, e.g. by conductors 87, to control circuitry 89 responsive to the first and second modes of the switch 81 to effect selected monitoring or control functions. For example, the control circuitry 89 may disable the sterilization apparatus or the venting capability of that apparatus during the second switch mode (at any time that the canister 11 is not properly positioned as shown by FIG. 3).

The number of vent (purge) cycles occurring with a canister 11 in place may be counted, with counting interrupted when the canister is removed. Counting may then resume from zero when a new canister is positioned within the receptacle 25. This counting is useful in monitoring the actual usage of a canister 11. Maintenance protocols typically require replacement of a canister 11 after a preselected time in service or number of cycles of use. The control functions of the control circuit (typically including a microprocessor) may be effected through conductors 91 connected to auxiliary standard devices in conventional fashion.

Reference in the specification to specific details of the illustrated embodiments is not intended to limit the scope of the appended claims.

We claim:

1. A filter apparatus for the vent stream of a sterilization apparatus comprising:
   a structural base with first and second mounting surfaces;
   an inlet chamber with a first end connected to said first mounting surface to form a well having a top openly communicating through said base and a bottom;
   an inlet conduit openly communicating through said bottom with said well, constituting means for delivering vent fluids to said well;
   a filter canister with a recessed inlet end and an outlet end, said canister containing filter medium and said inlet end being sealedly mounted to said second mounting surface to provide a travel path for vent fluids from said well, through said recessed inlet end, through said filter medium and out through said outlet end;
   a liquid trap filter mounted in said well in said travel path between said inlet conduit and said recessed inlet end; and
   a proximity switch mounted for actuation into a first mode when said canister is sealedly positioned on said structural base and for actuation into a second mode when said canister is removed from said structural base.

2. A filter apparatus according to claim 1 including control means in operable association with said switch and responsive to said first mode to effect enablement of said sterilization apparatus and to said second mode to effect disablement of said sterilization apparatus whereby said sterilization apparatus is operable to generate vent fluids only when said canister is sealedly positioned on said structure base.

3. A filter apparatus according to claim 1 wherein said liquid trap filter comprises a cellular foam element which occupies substantially the entire internal volume of said well.

4. A filter apparatus according to claim 3 including an annular sealing ring mounted approximately concentric with respect to said well between said structural base and said canister.

5. A filter apparatus according to claim 3 wherein said recessed inlet end forms an enclosure with said second mounting surface so that vent fluids exiting said fluid trap filter collect in said chamber prior to entering said inlet end of said canister.

6. A filter apparatus according to claim 4 wherein said recessed inlet end forms an enclosure with said second mounting surface so that vent fluids exiting said fluid trap filter collect in said chamber prior to entering said inlet end of said canister.

7. A filter apparatus according to claim 6 including control means in operable association with said switch and responsive to said first mode to effect enablement of said sterilization apparatus and to said second mode to effect disablement of said sterilization apparatus whereby said sterilization apparatus is operable to generate vent fluids only when said canister is sealedly positioned on said structural support.

8. A filter apparatus according to claim 6 including guide supports associated with said first mounting surface for receiving said canister constituting means for registering said recessed inlet end with said sealing ring.

9. A filter apparatus according to claim 8 wherein said liquid trap filter is constructed of a polyurethane foam.

10. A filter apparatus according to claim 8 wherein said liquid trap filter occupies a portion of said enclosure.

11. A filter apparatus according to claim 8 wherein said filter medium is potassium permanganate.

12. A filter apparatus according to claim 1 wherein said liquid trap filter comprises a cellular foam element which occupies substantially the entire internal volume of said well.

13. A filter apparatus according to claim 1 including an annular sealing ring mounted approximately concentric with respect to said well between said structural base and said canister.

14. A filter apparatus according to claim 1 wherein said recessed inlet end forms an enclosure with said second mounting surface so that vent fluids exiting said fluid trap filter collect in said chamber prior to entering said inlet end of said canister.

* * * * *